(12) United States Patent
Mangat et al.

(10) Patent No.: US 8,993,512 B2
(45) Date of Patent: Mar. 31, 2015

(54) COMPOSITIONS AND METHOD FOR TREATMENT OF ISCHEMIC NEURONAL REPERFUSION INJURY

(71) Applicant: Howard University, Washington, DC (US)

(72) Inventors: Harpal S. Mangat, Potomac, MD (US); Pradeep K. Karla, Arlington, VA (US)

(73) Assignee: Howard University, Washington, DC (US)

( * ) Notice: Subject to any disclaimer, the term of this patent is extended or adjusted under 35 U.S.C. 154(b) by 0 days.

(21) Appl. No.: 14/273,343

(22) Filed: May 8, 2014

(65) Prior Publication Data

US 2014/0336120 A1  Nov. 13, 2014

Related U.S. Application Data

(60) Provisional application No. 61/821,123, filed on May 8, 2013.

(51) Int. Cl.

| | |
|---|---|
| *A61K 38/00* | (2006.01) |
| *A61K 47/00* | (2006.01) |
| *A61K 31/4178* | (2006.01) |
| *C07D 405/12* | (2006.01) |
| *A61K 45/06* | (2006.01) |
| *A61K 38/05* | (2006.01) |
| *A61K 31/13* | (2006.01) |
| *A61K 31/40* | (2006.01) |
| *A61K 31/5513* | (2006.01) |
| *A61K 31/5517* | (2006.01) |

(52) U.S. Cl.
CPC .......... *A61K 31/4178* (2013.01); *C07D 405/12* (2013.01); *A61K 45/06* (2013.01); *A61K 38/05* (2013.01); *A61K 31/13* (2013.01); *A61K 31/40* (2013.01); *A61K 31/5513* (2013.01); *A61K 31/5517* (2013.01)
USPC .......................................................... 514/1.3

(58) Field of Classification Search
None
See application file for complete search history.

(56) References Cited

U.S. PATENT DOCUMENTS

| | | | |
|---|---|---|---|
| 2,990,402 | A | 6/1961 | Jack et al. |
| 4,433,684 | A | 2/1984 | Sarnoff et al. |
| 6,462,066 | B2 | 10/2002 | Mangat et al. |
| 7,758,890 | B2 | 7/2010 | Anderson et al. |
| 2001/0053790 | A1 | 12/2001 | Mangat et al. |
| 2004/0122015 | A1 | 6/2004 | Boykin et al. |
| 2006/0030548 | A1 | 2/2006 | Dong et al. |
| 2006/0178354 | A1 | 8/2006 | Lucas |
| 2007/0265296 | A1 | 11/2007 | Dalton et al. |
| 2008/0090808 | A1 | 4/2008 | Volvovitz |

OTHER PUBLICATIONS

PCT International Search Report and Written Opinion of the International Searching Authority dated Aug. 29, 2014 for International Application PCT/US2014/037359, 11 pages.
PCT International Search Report and Written Opinion of the International Searching Authority dated Sep. 4, 2014 for International Application PCT/US2014/037362, 17 pages.
Yasuhiro Tsume and Gordon L. Amidon, Selection of Suitable Prodrug Candidates for in vivo Studies via in vitro Studies; The Correlation of Prodrug Stability in Between Cell Culture Homogenates and Human Tissue Homogenates, Journal of Pharmacy & Pharmaceutical Sciences, 2012, vol. 15, No. 3, pp. 433-446.

*Primary Examiner* — Thomas S Heard
(74) *Attorney, Agent, or Firm* — Fitch, Even, Tabin & Flannery, LLP

(57) ABSTRACT

A method and composition for the treatment of ischemic neuronal reperfusion injury are provided. The composition can include a compound which is a combination of dantrolene and a residue of FMOC-valine. This composition can be used to provide a faster and higher CNS penetration than heretofore experienced with dantrolene. In another form, dantrolene may be formulated as a pro-drug, a pro-pro-drug and the like.

11 Claims, No Drawings

COMPOSITIONS AND METHOD FOR TREATMENT OF ISCHEMIC NEURONAL REPERFUSION INJURY

CROSS-REFERENCE TO RELATED APPLICATIONS

This application claims benefit of U.S. Provisional Application Ser. No. 61/821,123, filed on May 8, 2013, which is hereby incorporated herein by reference in its entirety.

FIELD

This application is directed to the treatment of and prevention of ischemic neuronal injuries.

BACKGROUND

Interruption of the blood supply to neural tissues, such as the brain, can cause a complex series of biochemical changes which may result in neuronal cell damage. At the cellular level, it is generally understood that damage is mediated by opening of the N-methyl-D-aspartate (NMDA) channels in the membrane. Further, ischemia begins when the blood supply stops or is significantly slowed, and this ischemia phase may be followed by restoration of the blood supply during a reperfusion phase. It is understood that cellular damage may occur during both phases, though they occur through different mechanisms.

There are a complex series of events which contribute to cell death during ischemia/reperfusion. Six substances that accumulate during ischemia include excitatory amino acids, intracellular calcium, arachidonic and other free fatty acids, hypoxanthine, xanthine oxidase, and platelet activating factor.

Ischemia triggers at least three pathways deleterious to the cell. First, a lack of oxygen depletes energy stores (principally adenosine diphosphate known as ATP). This disrupts homeostatic mechanisms, most importantly the membrane pump mechanism that maintains intracellular calcium at low levels. The resulting rise in intracellular calcium, which occurs principally because of the opening of the N-methyl-D-aspartate (NMDA) channels in the membrane, increases release of glutamic acid, activates destructive proteases and lipases, and indirectly converts the enzyme xanthine dehydrogenase to the potentially harmful xanthine oxidase. Second, excitatory amino acids ("excitotoxins"), principally glutamic and aspartic acids, are released, activate calcium channels, further increase intracellular calcium through a positive feedback mechanism, and allow cellular entry of excess water, sodium and chloride. Third, acidosis enhances destructive lipid peroxidation and the release of damaging free radicals.

Upon restoration of the blood supply, the reperfusion phase begins. An increased intracellular calcium level, a result of opened NMDA channels during ischemia, triggers a more destructive cascade. The initial calcium impulse causes a cascade which results in the release of intracellular calcium stores from the intravesicular calcium deposit. The release of intracellular calcium is mediated via the ryanodine receptor, principally the type 3 ryanodine receptor. The net result is a thirtyfold rise in intracellular calcium and cell death. Attempts have been made to reperfuse as soon as possible after the onset of ischemia, but it is important to note that the reperfusion itself causes the cascade, therefore the neurodestructive phases of ischemia and reperfusion are distinct.

Neurophysiologists view reperfusion injury as a cascade process that leads to excitotoxic cell death. The rise in intracellular calcium during reperfusion causes vasoconstriction of neighboring blood vessels. In addition, it causes the release of free oxygen radicals, in part from the action of xanthine oxidase. The net result is excitotoxic neuronal cell death.

Increased cytosolic $C_a^2+$ concentration contributes significantly to neuronal cell damage during ischemic reperfusion. U.S. Pat. No. 6,462,066 to Mangat et al. (which is incorporated herein as if fully rewritten) describes the above phenomena of ischemic injury and discusses the use of dantrolene to prevent or minimize neuronal cell damage that occurs during the reperfusion phase of an ischemic episode.

Dantrolene is an antagonist of the type 3 ryanodine receptor and is commonly given as the sodium salt (sodium dantrium), which is hydrated 1-[[[5-(4-nitrophenyl)2-furanyl]methylene]amino]-2,4-imidazolidinedione sodium salt. Dantrolene is prescribed in the treatment of clinical spasticity resulting from upper motor neuron disorders such as spinal chord injury, cerebral palsy, stroke, or multiple sclerosis. Dantrolene is also effective in reversing the hypermetabolic process of malignant hyperthermia, a genetic disorder of skeletal muscle that is triggered by exposure to anesthetics and certain relaxants.

The conflict in Iraq has produced an unprecedented number of traumatic brain injuries and has radically changed the way we treat trauma with the advent of Combat Surgical Hospitals on the frontline with injured troops arriving within an hour of injury. A patient might remain in the combat hospital for only six hours. The goal is lightning-swift, expert treatment, followed as quickly as possible by transfer to the military hospital in Landstuhl, Germany, for continued treatment.

American troops injured in Iraq have required limb amputations at twice the rate of past wars, and as many as 20 percent have suffered head and neck injuries that may require a lifetime of care. Accurate statistics are not yet available on recovery from this new round of battlefield brain (traumatic brain) injuries, an obstacle that frustrates combat surgeons. But judging by medical literature and surgeons' experience with their own patients some experts believe that three or four months from injury, 50 to 60 percent will be functional and doing things. In other words, these patients may be up and around, but with pretty significant disabilities, including paralysis. The remaining 40 percent to 50 percent of patients include those whom the surgeons send to Europe, and on to the United States, may have no prospect of regaining consciousness.

Preventing or minimizing neuronal cell damage that occurs during the reperfusion phase of an ischemic episode by virtue of a combat injury or other traumatic events which cause brain injuries or contusions with a non invasive administration of compounds which achieve higher and faster CNS penetration than dantrolene would be highly desirable and life saving.

Severe cerebral contusion is sometimes associated with early edema formation within 24-48 hours post-trauma, and this frequently results in progressive ICP (intracranial pressure) elevation, clinical deterioration and swelling. This swelling causes pressure on the brain squeezing it in the cranium (skull) and causing ischemic changes to the brain, often occluding fine blood supply to critical areas of the brain. Once steroids are on board to shrink the swelling there will be a secondary reperfusion injury as blood supply is re-established which contributes to further edema and neuronal cell death.

The mechanism of cell death for neurons is via the release of intracellular calcium. This leads to neuronal cell swelling/ death and edema. This pathway occurs both at initial ischemic insult and when the reperfusion injury occurs.

In another aspect, it has been recognized that certain nerve gasses based upon organophosphorus compounds, such as sarin, soman, tabun and cylcosarin (cyclohexyl methylphosphonofluoridate, a gas known as GF) cause ischemic injuries by generally the same mechanism as severe cerebral contusions. It has been found that the method of administration of dantrolene has not been successful in achieving effective neuroprotection against nerve gas attack.

SUMMARY

It has been found that a compound which is a combination of dantrolene and a residue of FMOC-valine (as shown in the general formulas I, II and III are set forth below), provides a faster and higher CNS penetration than heretofore experienced with dantrolene. In another form, dantrolene may be formulated as a pro-drug, a pro-pro-drug and the like.

general formula I

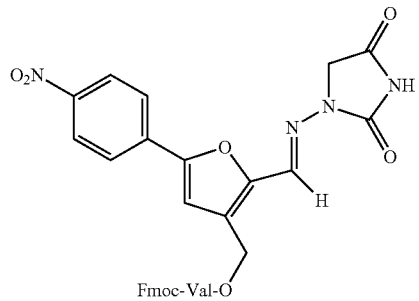
Fmoc-Val-O where FMOC-Val is the residue of FMOC-valine may be in the L or D form where FMOC-L-valine has the structure:

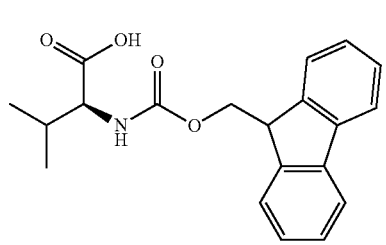 [SMILES: CC(C)[C@H](NC(=O)OCC1c2ccccc2-c2ccccc21)C(=O)O]

And where FMOC-D-valine has the structure:

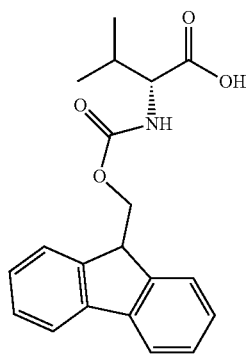 [SMILES: CC(C)[C@@H](NC(=O)OCC1c2ccccc2-c2ccccc21)C(=O)O]

The FMOC group may be removed as a "protective" group to provide general formula II

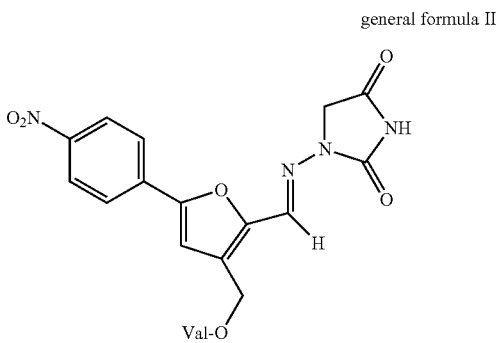
Val-O where "val" is a residue of $$\text{H}_3\text{C}\diagdown\text{CH}(\text{CH}_3)-\text{CH}(\text{NH}_2)-\text{COOH}$$

Third, a compound having the general formula III set forth below also may be used general formula III O$_2$N—[furan-phenyl-hydantoin structure]—Val-Val-O where val-val is a residue of

[dipeptide structure: valyl-valine]

The compound of general formula I may be made by the following synthesis.

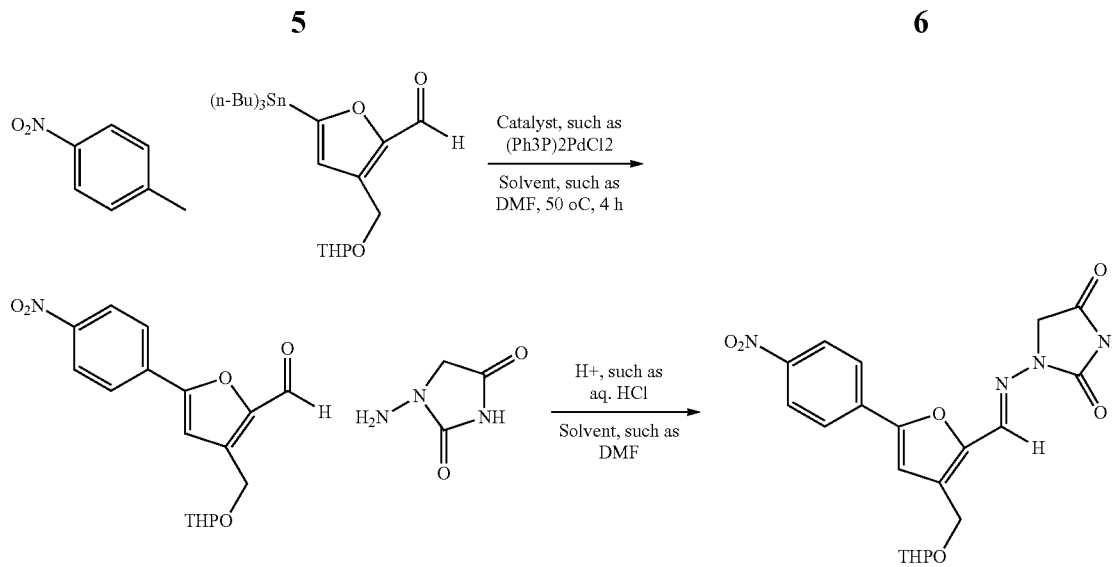

where THP is

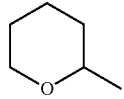

and THPO CH$_2$ is a residue of

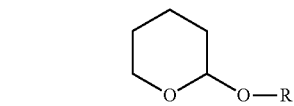

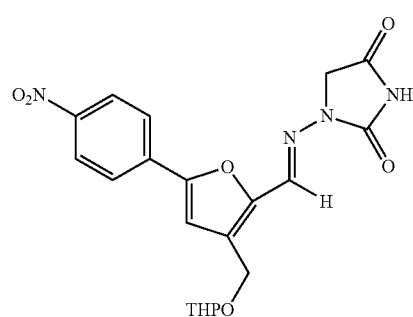

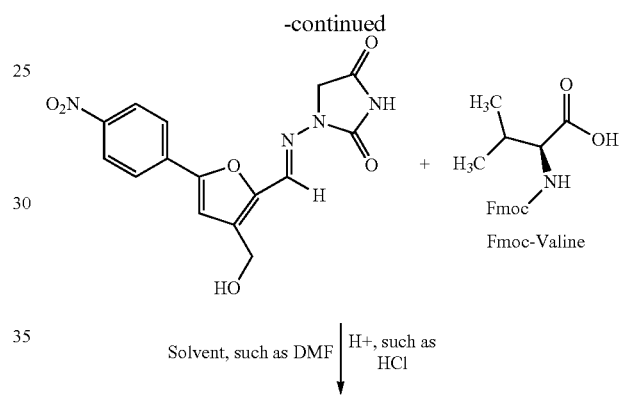

DETAILED DESCRIPTION

Compositions and methods for preparation for treatment of ischemic neuronal reperfusion are provided herein. Dantrolene may also be provided as dantrolene sodium and related compounds. For example, it may be provided in the form of 1-[[5-(p-nitrophenyl)furfurylidene]amino]hydantoin sodium hydrate.

In another form, dantrolene may be formulated as a pro-drug, a pro-pro-drug and the like. The compositions may be prepared with one or more active ingredients, such as the compounds of general formulas I, II and/or III.

general formula I

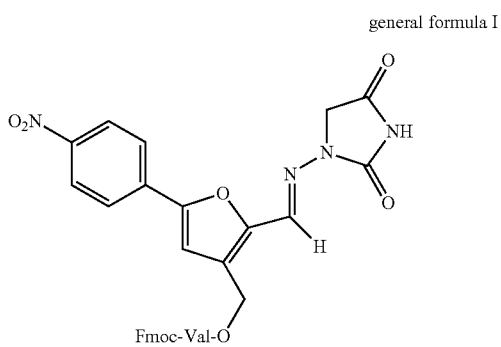

Fmoc-Val-O where FMOC-Val is the residue of FMOC-valine may be in the L or D form where FMOC-L-valine has the structure:

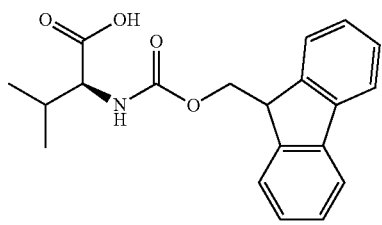 [SMILES: CC(C)[C@H](NC(=O)OCC1c2ccccc2-c2ccccc21)C(=O)O]

And where FMOC-D-valine has the structure:

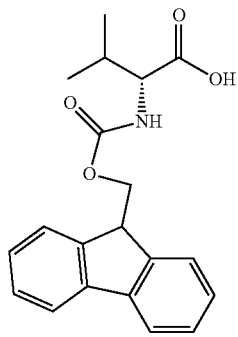 [SMILES: CC(C)[C@@H](NC(=O)OCC1c2ccccc2-c2ccccc21)C(=O)O]

The FMOC group may be removed as a "protective" group to provide general formula II

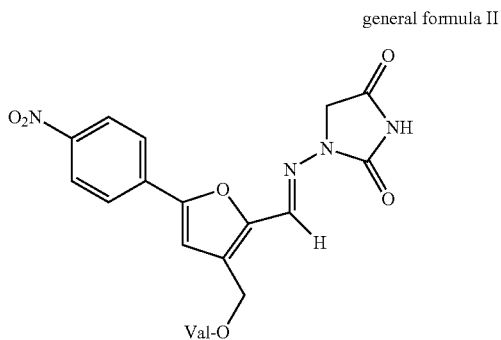

where "val" is a residue of

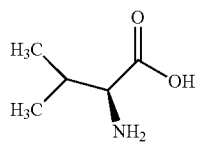

Third, a compound having the general formula III set forth below also may be used.

general formula III

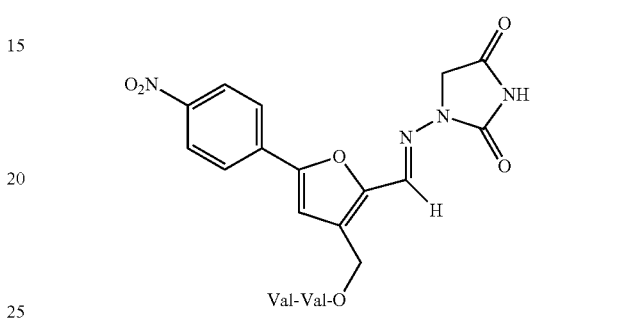

Val-Val-O

The compositions may also include pharmaceutically acceptable salts and can be administered alone or as an active ingredient in combination with pharmaceutically acceptable excipients, carriers, diluents, adjuvants and vehicles. For example, in one form, the compositions may be prepared in a nanoparticle emulsion form. The pharmaceutically acceptable excipients, carriers, diluents, adjuvants and vehicles, as well as implant carriers generally refer to inert, non-toxic solid or liquid fillers, diluents or encapsulating material not reacting with the active ingredients. The carrier can be a solvent or dispersing medium containing, for example, water, ethanol, polyol (for example glycerol, propylene, glycol, liquid polyethylene glycol, and the like), suitable mixtures thereof, vegetable oils, and aerosol mixtures. For example, some of the active ingredients may be included with Vitamins D, E and/or pluronic acid as dantrolene is highly soluble in these materials. Similarly, excipients and other materials may be used, such as discussed in EP 2583670, which is incorporated by reference herein.

In one form, val-dantrolene is dissolved in Vitamin E until saturation. In a separate container, dantrolene is dissolved with pluronic acid until saturation. The saturated Vitamin E and saturated pluronic acid components can then be mixed together with a suitable buffered saline solution by creating an emulsion suitable for administration.

In another form, val-dantrolene is dissolved in glycerin or Vitamin E until saturation. In a separate container, dantrolene is dissolved with polyethylene glycol/propylene glycol/pluronic acid until saturation. The two components can then be mixed together with a suitable buffered saline solution by creating an emulsion suitable for administration.

In one form, a rectal version of val-dantrolene that bypasses liver first pass metabolism may be used. According to one form, val-dantrolene is dissolved in glycerin or Vitamin E until saturation is reached. In a separate container dantrolene is dissolved with polyethylene glycol/propylene glycol/pluronic acid until saturation is reached. The saturated Vitamin E and saturated pluronic acid is then mixed together and mixed with a suitable buffered normal saline solution creating an emulsion with a pH of 7.4.

While compounds selected from the group of the general formulas I, II, III, and mixtures thereof, should be administered such that it is not extensively metabolized or exposed to direct renal elimination or excessive first pass effect of the liver, it may be administered orally, subcutaneously, parenterally, intravenously, intranasally, intrathecally, sublingually, rectally, topically, and the like.

When administering the active ingredients, the compounds can be formulated in a unit dosage in a variety of forms such as a solution, suspension or emulsion. The pharmaceutical formulations also include sterile aqueous solutions or dispersions, and sterile powders for reconstitution into sterile solutions or dispersions.

In a particularly important aspect, compounds selected from the group of formulas I, II, III, and mixtures thereof, may be administered through the lungs such as with a nebulizer (such as an ultrasonic and compressor nebulizer), gas mask, a gas masked with a nebulizer, a CPAP machine, an APAP machine and the like. The compound of formulas I, II and/or III will be particularly useful for administration through the lungs or intranasally because current dantrolene preparations contain sodium hydroxide which would have a deleterious effect on the lungs. In a particularly important aspect, the compounds are administered intranasally with a positive pulsating pressure with pulses occurring about every 5 seconds to 3 minutes.

The active ingredients, including compounds I, II and/or III can be administered in a variety of different dosages and intervals as appropriate. The doses may be single doses or multiple doses over a period of several days. The treatment generally has a length dependent upon the length of the disease process, drug effectiveness and the patient being treated. According to one form, after the initial loading in the first 8 hours, the compositions are then administered every 8 hours. In one form, 2-3 mg/kg is given every 2 hours for 6 hours and then every 8 hours.

In one form, the active ingredient is provided in a dosage range of about 100 ng/kg to about 100 mg/kg per day. In one form, the dosage is provided in a range of about 1 mg/kg to about 10 mg/kg per day. It should be noted that lower dosages of the active ingredient may be provided while still being at least as effective relative to dantrolene being administered the same way with the same frequency.

In yet another form, dantrolene, val-dantrolene, val-val-dantrolene and the like can be prepared in a powdered form. More specifically, the active ingredients can be formulated into optimally sized particles, such as 1-3 microns, through a liposomal or powder technique to permit the powder to be delivered efficiently into the lungs. Glass stabilization can be used for keeping the powders stable at room temperatures without the need for refrigeration. These powders can be in the form of blister packs.

The active ingredients may be formed in a variety of manners. In one form, the compound of general formula I may be made by the following synthesis.

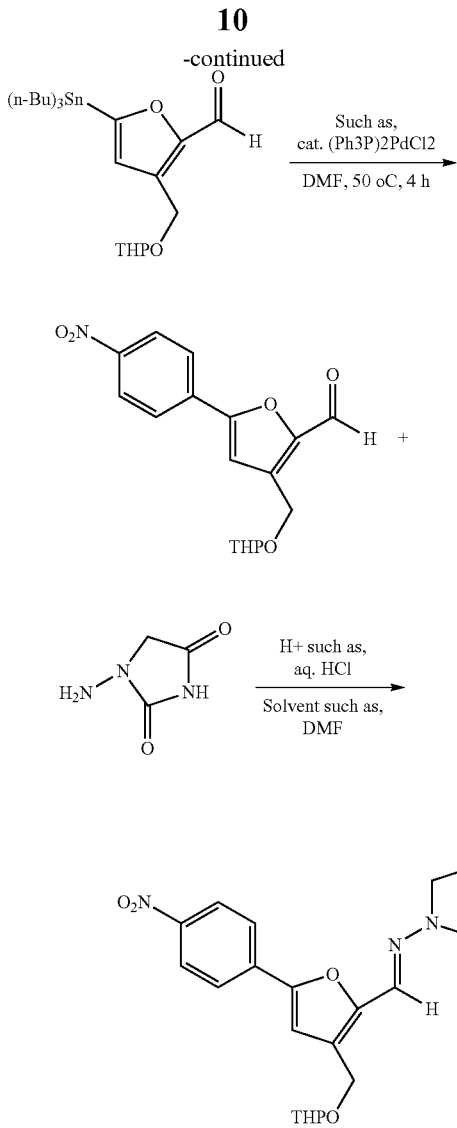

where THP is

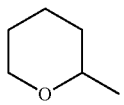

and THPO CH$_2$ is a residue of

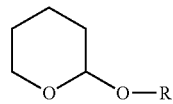

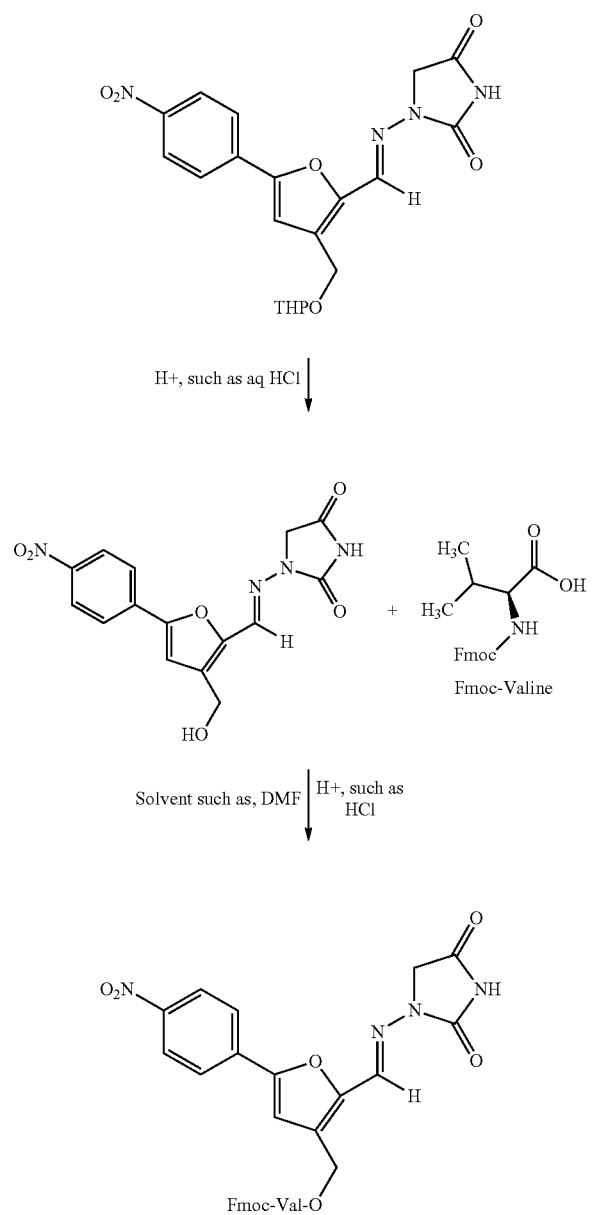

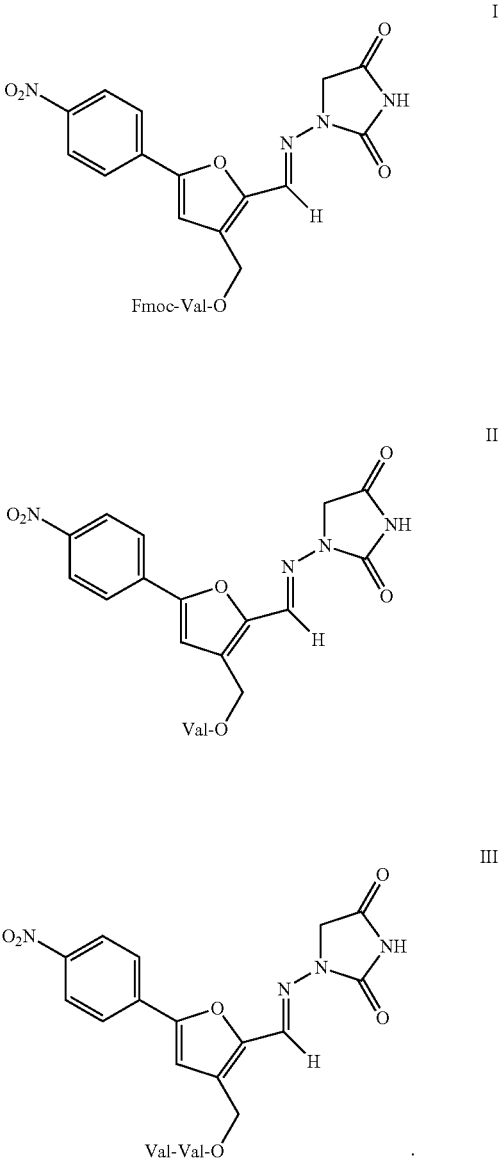

In one form, the composition can be administered for a variety of ischemic injury related conditions, such as those described above. Further, the compositions can be administered for other ischemic-type conditions including, but not limited to, neuroprotecting against loss of neurological/cognitive function after coronary bypass surgery, stroke, dementia, and the like. The compositions can be used to protect both the dying cells in the umbria and prevent spread into the penumbra.

While the compositions and uses have been particularly described with specific reference to particular process and product embodiments, it will be appreciated that various alterations, modifications, and adaptations may be based on the present disclosure, and are intended to be within the spirit and scope of the invention as defined by the following claims.

What is claimed is:

1. A method of treatment of neuronal reperfusion injury with ischemic neuropathy, the method comprising: administering an effective amount of at least one of a compound having the formulas I, II or III 2. The method of claim 1 wherein the at least one compound is administered in combination with at least one of Vitamin D, Vitamin E and pluronic acid.

3. The method of claim 1 wherein the at least one compound is in the form of a suspension or emulsion.

4. The method of claim 1 wherein the at least one compound is delivered to a patient via an administration selected from the group consisting of orally, subcutaneously, parenterally, intravenously, intranasally, intrathecally, sublingually, rectally, and topically.

5. The method of claim 1 wherein the at least one compound is administered in a dosage of about 100 ng/kg per day to about 100 mg/kg per day.

6. A compound having the general formulas I, II or III

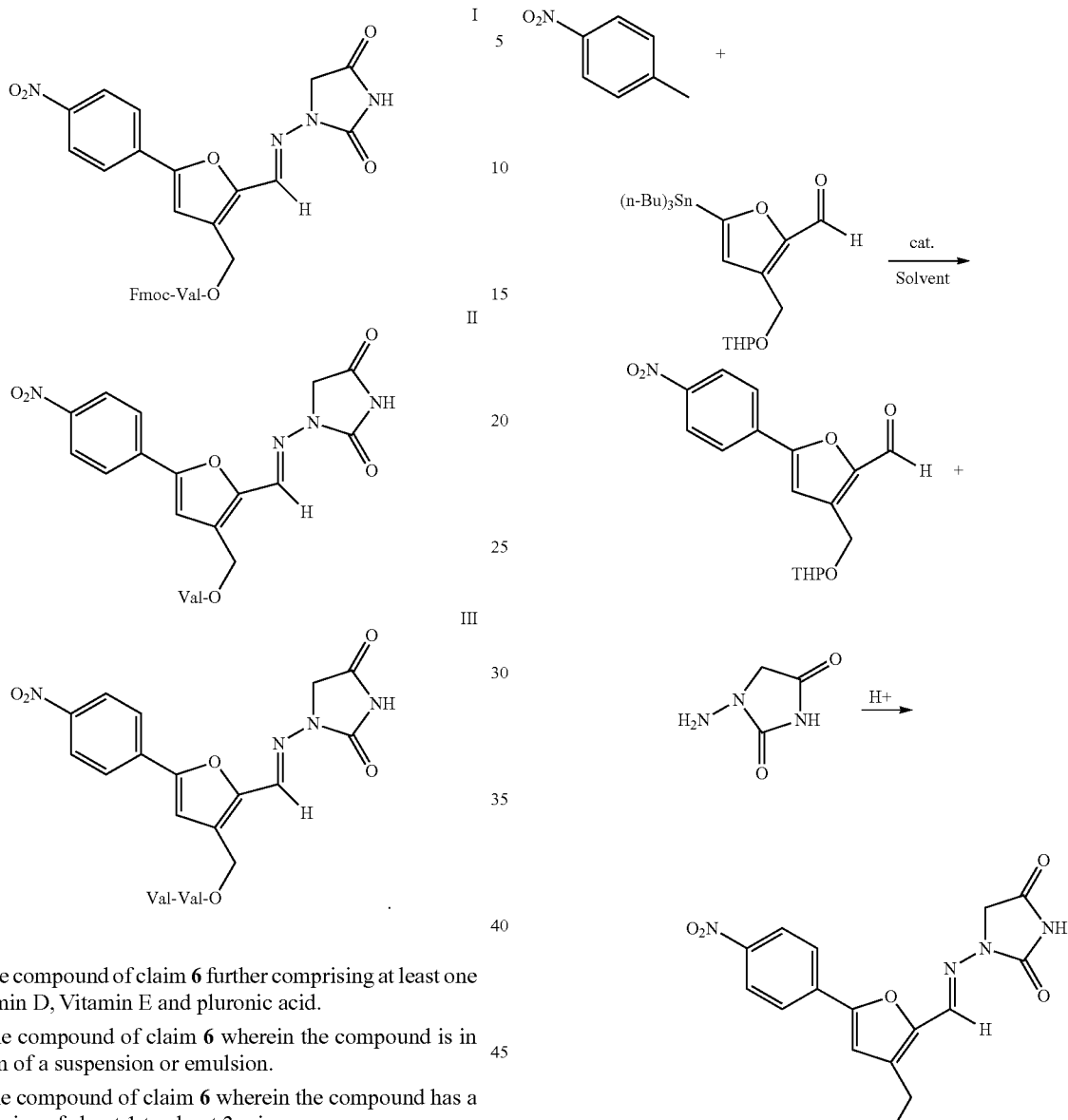

7. The compound of claim 6 further comprising at least one of Vitamin D, Vitamin E and pluronic acid.

8. The compound of claim 6 wherein the compound is in the form of a suspension or emulsion.

9. The compound of claim 6 wherein the compound has a particle size of about 1 to about 3 microns.

10. A method of making a compound having the formula

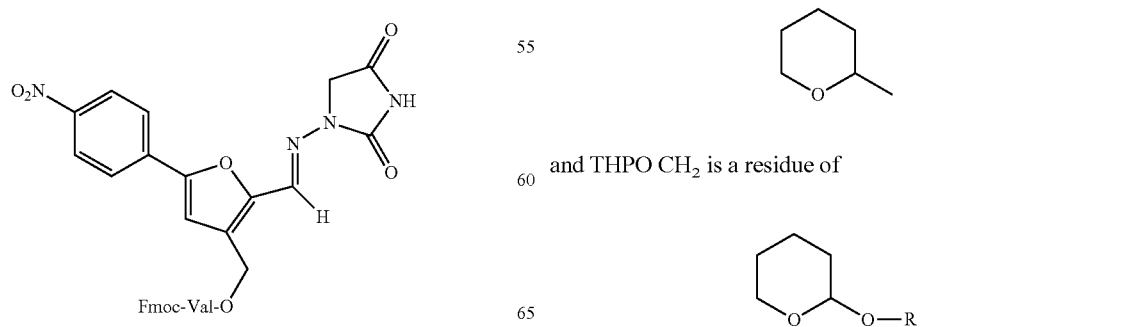

wherein the method comprises where THP is and THPO CH$_2$ is a residue of

15
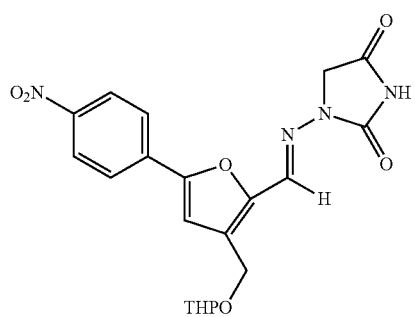
H+ ↓
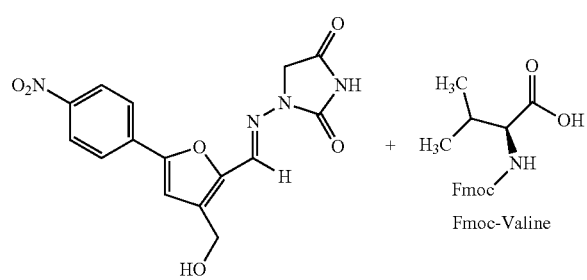
Solvent | H+ ↓
16
-continued
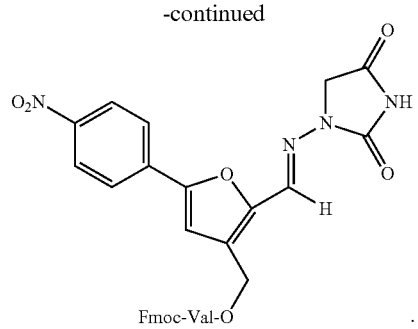
11. The method of claim 10 further comprising the step of combining
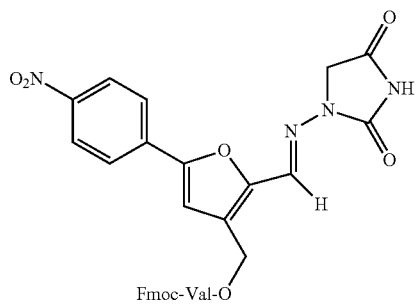
with at least one of Vitamin D, Vitamin E and pluronic acid.
* * * * *